US008710033B2

(12) United States Patent
Shiotani et al.

(10) Patent No.: US 8,710,033 B2
(45) Date of Patent: Apr. 29, 2014

(54) USE OF LPA FOR ENCOURAGING PREGNANCY, AND FERTILITY AGENT

(75) Inventors: Masahide Shiotani, Hyogo (JP); Sakae Goto, Osaka (JP); Mitsuo Shimizu, Hyogo (JP)

(73) Assignees: JCR Pharmaceuticals Co., Ltd., Ashiya-shi (JP); Masahide Shiotani, Kobe-shi (JP); Sakae Goto, Takatsuki-shi (JP)

( * ) Notice: Subject to any disclaimer, the term of this patent is extended or adjusted under 35 U.S.C. 154(b) by 0 days.

(21) Appl. No.: 13/392,133

(22) PCT Filed: Aug. 25, 2010

(86) PCT No.: PCT/JP2010/064361
§ 371 (c)(1),
(2), (4) Date: May 8, 2012

(87) PCT Pub. No.: WO2011/024850
PCT Pub. Date: Mar. 3, 2011

(65) Prior Publication Data
US 2012/0220553 A1    Aug. 30, 2012

(30) Foreign Application Priority Data

Aug. 26, 2009    (JP) .................................. 2009-195440

(51) Int. Cl.
*A61K 31/66*    (2006.01)
(52) U.S. Cl.
USPC ......................................................... 514/120
(58) Field of Classification Search
USPC ......................................................... 514/120
See application file for complete search history.

(56) References Cited

U.S. PATENT DOCUMENTS

| 6,949,528 B1 * | 9/2005 | Goddard et al. ................. 514/75 |
| 2010/0003339 A1 | 1/2010 | Shiotani et al. |

FOREIGN PATENT DOCUMENTS

| WO | WO 02/092104 | 11/2002 |
| WO | WO 2008/016039 A1 | 2/2008 |

OTHER PUBLICATIONS

International Search Report of PCT/JP2010/064361 (Oct. 28, 2010).
K. Hama et al., "Embryo Spacing and Implantation Timing are Differentially Regulated by LPA3-Mediated Lysophosphatidic Acid Signaling in Mice", Biology of Reproduction, vol. 77, No. 6 (2007) pp. 954-959.
A. Tokumura et al., "Hoon Kessho Oyobi Ranhoeki ni Sonzai suru Lysophosphatidic Acid no Seisei Kiko", Proceedings of Japanese Conference on the Biochemistry of Lipids, vol. 36 (1994) pp. 23-26.
M.C.W. Scholtes et al., "Blastocyst Transfer in Day-5 Embryo Transfer Depends Primarily on the Number of Oocytes Retrieved and Not on Age", Fertility and Sterility, vol. 69, No. 1 (Jan. 1998) pp. 78-83.
D.K. Gardner et al., "A Prospective Randomized Trial of Blastocyst Culture and Transfer in In-Vitro Fertilization", Human Reproduction, vol. 13, No. 12 (1998) pp. 3434-3440.
I.C. Chen et al., "Enhancement of Embryo Implantation Ability by LPA Supplementation through RGS2 Signaling Pathway", Human Reproduction (Oxford) vol. 22, Suppl. 1 (2007) pp. I211-I214, p. 545.
X. Ye et al., "LPA3-Mediated Lysophosphatidic Acid Signalling in Implantation and Embryo Spacing", Nature, vol. 435 (May 5) pp. 104-108.
S. Goto et al., "Stimulation of Endometrium Embryo Transfer (SEET): Injection of Embryo Culture Supernatant into the Uterine Cavity Before Blastocyst Transfer can Improve Implantation and Pregnancy Rates", Fertility and Sterility, vol. 88, No. 5 (Nov. 2007) pp. 1339-1343.
R.G. Edwards et al., "Blastocyst Stage Transfer: Pitfalls and Benefits", Human Reproduction, vol. 14, No. 1 (1999) pp. 1-6.
D.K. Gardner et al., "Culture and Transfer of Human Blastocysts Increases Implantation Rates and Reduces the Need for Multiple Embryo Transfers", Fertility and Sterility, vol. 69, No. 1 (Jan. 1998) pp. 84-88.
A.A. Milki et al., "Two-Blastocyst Transfer has Similar Pregnancy Rates and a Decreased Multiple Gestation Rate Compared with Three-Blastocyst Transfer", Fertility and Sterility, vol. 72, No. 2 (Aug. 1999) pp. 225-228.
K.V. Sheth et al., "Prediction of Successful Embryo Implantation by Measuring Interleukin-1-Alpha and Immunosuppressive Factor(s) in Preimplantation Embryo Culture Fluid", Fertility and Sterility, vol. 55, No. 6 (May 1991) pp. 952-957.
L.C. Giudice, "Endometrial Growth Factors and Proteins", Seminars in Reproductive Endocrinology, vol. 13, No. 2 (May 1995) pp. 93-101.
K. Wakuda et al., "Embryo-Dependent Induction of Embryo Receptivity in the Mouse Endometrium", Journal of Reproduction and Fertility, vol. 115 (1999) pp. 315-324.
S. Perrier d'Hauterive et al., "Human Chorionic Gonadotropin and Growth Factors at the Embryonic-Endometrial Interface Control Leukemia Inhibitory Factor (LIF) and Interleukin 6 (IL-6) Secretion by Human Endometrial Epithelium", Human Reproduction, vol. 19, No. 11 (2004) pp. 2633-2643.
P. Licht et al., "On the Role of Human Chorionic Gonadotropin (hCG) in the Embryo-Endometrial Microenvironment: Implications for Differentiation and Implantation", Seminars in Reproductive Medicine, vol. 19, No. 1 (2001) pp, 37-47.
R.I. Baranao et al., "Determination of IL-1 and IL-6 Levels in Human Embryo Culture-Conditioned Media", American Journal of Reproductive Immunology, vol. 37 (1997) pp. 191-194.

(Continued)

*Primary Examiner* — Brandon Fetterolf
*Assistant Examiner* — Christopher R Stone
(74) *Attorney, Agent, or Firm* — Millen, White, Zelano & Branigan, P.C.

(57) ABSTRACT

The objective is to find compounds which have an activity to improve the success rate of pregnancy and implantation in blastocyst transfer in mammals, to provide a method of producing and using the compounds, and to provide a pregnancy-promoting agent. Disclosed is a pregnancy-promoting agent containing one or more lysophosphatidic acids selected from the group consisting of LPA-C16:0, LPA-C16:1, LPA-C18:0, LPA-C18:1 and LPA-C18:2.

3 Claims, 15 Drawing Sheets

(56) References Cited

OTHER PUBLICATIONS

M.J. De Los Santos et al., "Expression of Interleukin-1 System Genes in Human Gametes", Biology of Reproduction, vol. 59 (1998) pp. 1419-1424.

C. Simon et al., "Embryonic Regulation of Integrins β3, α4, and α1 in Human Endometrial Epithelial Cells In Vitro", Journal of Clinical Endocrinology and Metabolism, vol. 82, No. 8 (1997) pp. 2607-2616.

S.I. Tazuke et al., "Growth Factors and Cytokines in Endometrium, Embryonic Development, and Maternal: Embryonic Interactions", Seminars in Reproductive Endocrinology, vol. 14, No. 3 (Aug. 1996) pp. 231-245.

A. Jurisicova et al., "Variability in the Expression of Trophectodermal Markers β-Human Chorionic Gonadotrophin, Human Leukocyte Antigen-G and Pregnancy Specific β-1 Glycoprotein by the Human Blastocyst", Human Reproduction, vol. 14, No. 7 (1999) pp. 1852-1858.

\* cited by examiner

USE OF LPA FOR ENCOURAGING PREGNANCY, AND FERTILITY AGENT

TECHNICAL FIELD

The present invention relates to a composition which promotes pregnancy in fertility treatment in mammals by blastocyst transfer, a method for production of the same, and a method for promoting pregnancy using the composition.

BACKGROUND ART

Infertility in humans is said to be observed around 10% of the couples. Therefore, there have been significant needs for fertility treatment, and by now, it is commonly practiced. Among different current methods of fertility treatment, those in which sperm cells or eggs are directly handled are known as artificial insemination and in vitro fertilization, respectively. Artificial insemination is a technique to promote pregnancy by injecting sperm cells into the vagina at a position close to the cervix, or directly into the uterus or the oviducts, using an instrument such as catheter and the like, and it aims to increase the success rate of fertilization, by artificially conducting a process which then leads sperm cells to meet an egg. On the other hand, in vitro fertilization is a technique by which a patient is administered an ovulation inducer to induce generation of ova, which then are collected out of the body and mixed with sperm cells in a test tube to have them got fertilized, and the fertilized eggs then are cultured and, generally on days 2-3 of culture, embryos at the 4- or 8 cell stage are transferred, generally into the uterine cavity, with a catheter. In order to make the implantation of the transferred embryos easier, administration of luteinizing hormone is usually carried out in order to condition the uterine endometrium.

A preimplantation embryo produces several factors during its development to signal its presence to the maternal organism. Interleukin-1 (IL-1), for example, is a primary factor which modulates cross talks between the embryo and the uterine endometrium of the maternal organism, and the IL-1 system is found at all the stages of development (Non-Patent Literature 1). With regard to human chorionic gonadotropin (hCG), another of the embryonic factors, expression of its gene can be found to occur already in the 2-cell stage embryo (Non-Patent Literature 2). It also is observed that several embryonic factors, including the above two, involved in the cross talks are released out of the cells when an embryo is cultured in vitro (in a test tube). Namely, several embryonic factors that modulate endometrial receptivity are detectable in the supernatant of embryo cultures (Non-Patent Literatures 3-9). It is known that, in vivo also, an embryo developing in the oviduct induces differentiation of the uterine endometrium (Non-Patent Literature 10). All these facts, taken together, indicate that the cross talks take place via the factors produced by the embryo between the embryo and the uterine endometrium, at the early stages of embryonic development. In fact, it has been shown that not only a preimplantation embryo in the uterine cavity, but even an early embryo still remaining in the oviduct has the ability to modulate certain molecules in the uterine endometrium to place its implantation under its own control (Non-Patent Literature 10).

In recent years, blastocyst transfer, which is a technique of in vitro fertilization performed as fertility treatment, has been proposed and practiced clinically as a means of improving the success rate of implantation in human fertility treatment (Non-patent Literatures 11-13). In this technique, embryos produced by in vitro fertilization as described above are cultured for 5 to 6 days to let them develop into blastocysts, which then are injected into the uterine cavity. Employing the technique of blastocyst transfer, higher implantation rates are achieved compared with transferring embryos which are at earlier stages, for the former has such advantages that it allows physiological synchronization of the uterine endometrium with the developmental stage of the embryos, as well as relatively easier selection of embryos with higher ability for implantation owing to a longer in vitro culture (Non-Patent Literatures 14 and 15). Even so, however, the success rate of pregnancy by blastocyst transfer actually remains at a low level of about 36.4%. Unsuccessful implantation after blastocyst transfer is thought to be due, e.g., to failure of the blastocyst to escape from the zona pellucida or to arrested development of the transplanted blastocyst in the uterine cavity. Further, lack of cross talks between the uterine endometrium and the embryo at the development stages from early embryo to blastocyst is thought to be another cause of failure. This lack of exchange of information can be a cause of insufficient modulation of the uterine endometrium's receptivity to embryos.

In order to increase the success rate of pregnancy in blastocyst transfer, a method has been developed in which the supernatant of a culture obtained by culturing a human embryo in a medium until it develops into a blastocyst is injected into the uterine cavity prior to the transfer of a blastocyst into the uterus [SEET (Stimulation of Endometrium Embryo Transfer) therapy]. According to this method, 90% or greater success rate of pregnancy is achieved (Non-Patent Literature 16 and Patent Literature 1). This improvement in the success rate of pregnancy by SEET therapy suggests that the supernatant of the culture which is injected into the uterine cavity contains some active ingredient which can improve success rate of pregnancy. However, it is not known what such active ingredient is.

Though phospholipids generally have two fatty acid moieties, certain phospholipids occuring in the living body have no more than one fatty acid moiety. They are called "lysophospholipids". Lysophosphatidic acid, one of known lysophospholipids, corresponds to 1-acylglycerol 3-phosphate or 2-acylglycerol 3-phosphate. It is commonly known that various lysophosphatidic acids differing from one another in their fatty acid moieties occur in the living body and that they have physiological activities, such as promotion of cellar growth, for example. Lysophosphatidic acids exert their activities mainly through cell surface receptors, of which at least 4 types are known ($LPA_1$, $LPA_2$, $LPA_3$, and $LPA_4$). Though a study on mice lacking the gene of one of these lysophosphatidic acid receptors, LPA3, has shown that signal transduction via $LPA_3$ plays an important role in implantation of a fertilized egg (Non-Patent Literature 17), it is not known which of the phosphatidic acids involved.

CITATION LIST

Patent Literature

[PL1] WO2008/016039

Non Patent Literature

[NPL 1] Del los Santos MJ. et. al., Biol Reprod. (1998) 59, 1419-1424
[NPL 2] Jurisicova A. et al., Hum Reprod. (1999) 14, 1852-1858
[NPL 3] Tanzuke SI. et. Al., Semin Reprod Endocrinol. (1996) 14, 231-245

[NPL 4] Simon C. et. al., Clin Endocrinol Metab. (1997) 82, 2607-2616
[NPL 5] Giudice L C. et.al., Semin Reprod Endocrinol.(1995) 13, 93-101
[NPL 6] Sheth K V. et.al., Fertil Steril. (1991) 55, 952-957
[NPL 7] Baranao R I. et.al.,Am J Reprod Immunol. (1997) 37, 191-194
[NPL 8] Licht P. et.al., Semin Reprod Med. (2001) 19, 37-47
[NPL 9] Perrier d'Hauterive. et.al., Hum Reprod. (2004) 19, 2633-2643
[NPL 10] Wakuda K. et.al., Reprod Fertil. (1999) 115, 315-324
[NPL 11] Gardner D K. et.al., Hum Reprod. (1998) 13, 3434-3440
[NPL 12] Scholtes M C. et.al., Fertil Steril. (1998) 69, 78-83
[NPL 13] Milki A A. et.al., Fertil Steril. (1999) 72, 225-228
[NPL 14] Gardner D K. et.al., Fertil Steril. (1998) 69, 84-88
[NPL 15] Edwards R G. et.al., Hum Reprod. (1999) 14, 1-4
[NPL 16] Goto S. et.al., Fertil Steril. (1999) 88, 1339-1343
[NPL 17] Yo X. et.al., Nature (2005) 435, 104-108

SUMMARY OF INVENTION

Technical Problems

Against the above background, the objective of the present invention is to find a compound which has an activity to improve the success rate of implantation and pregnancy in patients undergoing blastocyst transfer, and to provide methods for its production and use, as well as an agent for promoting pregnancy.

Technical Solution

In SEET therapy, by which the success rate of pregnancy in humans undergoing blastocyst transfer can be improved from the current figures staying around 36% to 90% or more, the supernatant of a culture which is obtained by culturing human embryos in a medium until they develop into blastocysts is injected into the uterine cavity prior to implantation of the embryos in the uterus. The present inventors assumed that there are contained some active ingredient in the culture supernatant which can improve the success rate of pregnancy. Upon this assumption, the present inventors, having analyzed the culture supernatant using chromatography and mass spectrometry, found that no such protein was detected in the culture supernatant as coming from the human embryo and having an activity capable of influencing on implantation of a transferred blastocyst and pregnancy, and that the only ingredients originating from the human embryos detected in the culture supernatant were five different lysophosphatidic acids. The present invention was completed as a result of further studies based on this finding.

Thus, the present invention provides what follows.

1. A pregnancy-promoting agent for promoting pregnancy of a patient undergoing blastocyst transfer, comprising one or more lysophosphatidic acids.
2. The pregnancy-promoting agent according to 1 above, wherein the lysophosphatidic acid is one or more selected from the group consisting of LPA-C16:0, LPA-C16:1, LPA-C18:0, LPA-C18:1 and LPA-C18:2.
3. The pregnancy-promoting agent according to 1 above, wherein the lysophosphatidic acids are LPA-C16:0, LPA-C16:1, LPA-C18:0, LPA-C18:1 and LPA-C18:2.
4. The pregnancy-promoting agent according to 3 above, wherein the mutual proportion of the content of LPA-C16:0, LPA-C16: 1, LPA-C18:0, LPA-C18:1 and LPA-C18:2 is 36-66:1-2:5-10:13-25:15-28 in molar ratio.
5. The pregnancy-promoting agent according to 3 above, wherein 98-182 pmol of LPA-C16:0, 2.8-5.2 pmol of LPA-C16:1, 14-26 pmol of LPA-C18:0, 36-68 pmol of LPA-C18:1, and 40-76 pmol of LPA-C18:2 are injected into the uterine cavity of the patient at one time of administration.
6. The pregnancy-promoting agent according one of 1 to 5 above, which is administered prior to the transfer of a blastocyst.
7. A method for production of lysophosphatidic acid comprising the steps of culturing an embryo of a mammalian animal in a medium, and collecting the supernatant of thus obtained culture.
8. The method for production according to 7 above, wherein the lysophosphatidic acid is one or more selected from the group consisting of LPA-C16:0, LPA-C16:1, LPA-C18:0, LPA-C18:1 and LPA-C18:2.
9. The method according to 7 or 8 above, wherein the mammalian animal is a human.
10. The method according to one of 7 to 9 above, wherein the medium is a serum-free medium.
11. A method for promoting pregnancy in blastocyst transfer comprising administering an effective amount of one or more lysophosphatidic acids into the uterine cavity of a patient.
12. The method according to 11 above, wherein the lysophosphatidic acid is one or more selected from the group consisting of LPA-C16:0, LPA-C16:1, LPA-C18:0, LPA-C18:1 and LPA-C18:2.
13. The method according to 11 above, wherein the lysophosphatidic acids are LPA-C16:0, LPA-C16:1, LPA-C18:0, LPA-C18:1 and LPA-C18:2.
14. The method according to 13 above, wherein the mutual proportion of the content of LPA-C16:0, LPA-C16:1, LPA-C18:0, LPA-C18:1 and LPA-C18:2 is 36-6:1-2:5-10:13-25:15-28 in molar ratio.
15. The method according to 13 above, wherein 98-182 pmol of LPA-C16:0, 2.8-5.2 pmol of LPA-C16:1, 14-26 pmol of LPA-C18:0, 36-68 pmol of LPA-C18:1, and 40-76 pmol of LPA-C18:2 are injected into the uterine cavity of the patient at one time of administration.
16. The method according to 11 above, wherein the lysophosphatidic acids are administered prior to the transfer of a blastocyst.

Advantageous Effect of Invention

The pregnancy-promoting agent according to the present invention described above, when injected into the uterine cavity prior to the transfer of a blastocyst into the uterus of the recipient of the embryo, remarkably increases the success rate of implantation of the transferred blastocyst and pregnancy.

BRIEF DESCRIPTION OF DRAWINGS

[FIG. 1-2] A chart showing the result of GC-MS (SCAN) analysis of a LPA-C18:1 standard sample. (C) GC-MS (Scan) analysis at the retention time of 16.33 min (Range scanned: m/z value of 35-800).

[FIG. 2-1] A chart showing the result of GC-SIM analysis of LPA-C16:0 in the sample. (A) GC-SIM analysis at the m/z value of 299.1, (B) GC-SIM analysis at the m/z value of 611.3.

[FIG. 2-2] A chart showing the result of GC-MS (SCAN) analysis of LPA-C16:0 in the sample. (C) GC-MS (Scan) analysis at the retention time of 15.31 min (Range scanned: m/z value of 35-800).

[FIG. 3-1] A chart showing the result of GC-SIM analysis of LPA-C16:1 in the sample. (A) GC-SIM analysis at the m/z value of 299.1. (B) GC-SIM analysis at the m/z value of 609.3.

[FIG. 3-2] A chart showing the result of GC-MS (SCAN) analysis of LPA-C16:1 in the sample. (C) GC-MS (Scan) analysis at the retention time of 15.20 min (Range scanned: m/z value of 35-800).

[FIG. 4-1] A chart showing the result of GC-SIM analysis of LPA-C18:0 in the sample. (A) GC-SIM analysis at m/z of 299.1, (B) GC-SIM analysis at m/z of 639.4

[FIG. 4-2] A chart showing the result of GCMS (SCAN) analysis of LPA-C18:0 in the sample. (C) GC-MS (Scan) analysis at the retention time of 16.58 min (Range scanned: m/z value of 35-800).

[FIG. 5-1] A chart showing the result of GC-SIM analysis of LPA-C18:1 in the sample. (A) GC-SIM analysis at the m/z value of 299.1. (B) GC-SIM analysis at the m/z value of 637.3.

[FIG. 5-2] A chart showing the result of GC-MS (Scan) analysis of LPA-C18:1 in the sample. (C) GC-MS (Scan) analysis at the retention time of 16.39 min (Range scanned: m/z value of 35-800).

[FIG. 6-1] A chart showing the result of GC-SIM analysis of LPA-C 18:2 in the sample. (A) GC-SIM analysis at the m/z value of 299.1. (B) GC-SIM analysis at the m/z value of 635.3.

[FIG. 6-2] A chart showing the result of GC-MS (SCAN) analysis of LPA-C18:2 in the sample. (C) GC-MS (Scan) analysis at the retention time of 16.35 min (Range scanned: m/z of 35-800).

[FIG. 7-1] A chart showing the result of GC-SIM analysis of a blank solution. Showing the result of GC-SIM analysis (A) at the m/z value of 299.1, and (B) at the m/z value of 611.3. An arrowhead indicates the retention time at which the corresponding ion for detection is to be seen.

[FIG. 7-2] A chart showing the result of GC-SIM analysis of a blank solution. Showing the result of GC-SIM analysis (C) at the m/z value of 609.3, and (D) at the m/z value of 639.4. An arrowhead indicates the retention time at which the corresponding ion for detection is to be seen.

[FIG. 7-3] A chart showing the result of GC-SIM analysis of a blank solution. Showing the result of GC-SIM analysis (E) at the m/z value of 637.3 and (F) at the m/z value of 635.3. An arrowhead indicates the retention time at which the corresponding ion for detection is to be seen.

DESCRIPTION OF EMBODIMENTS

Figure 1:
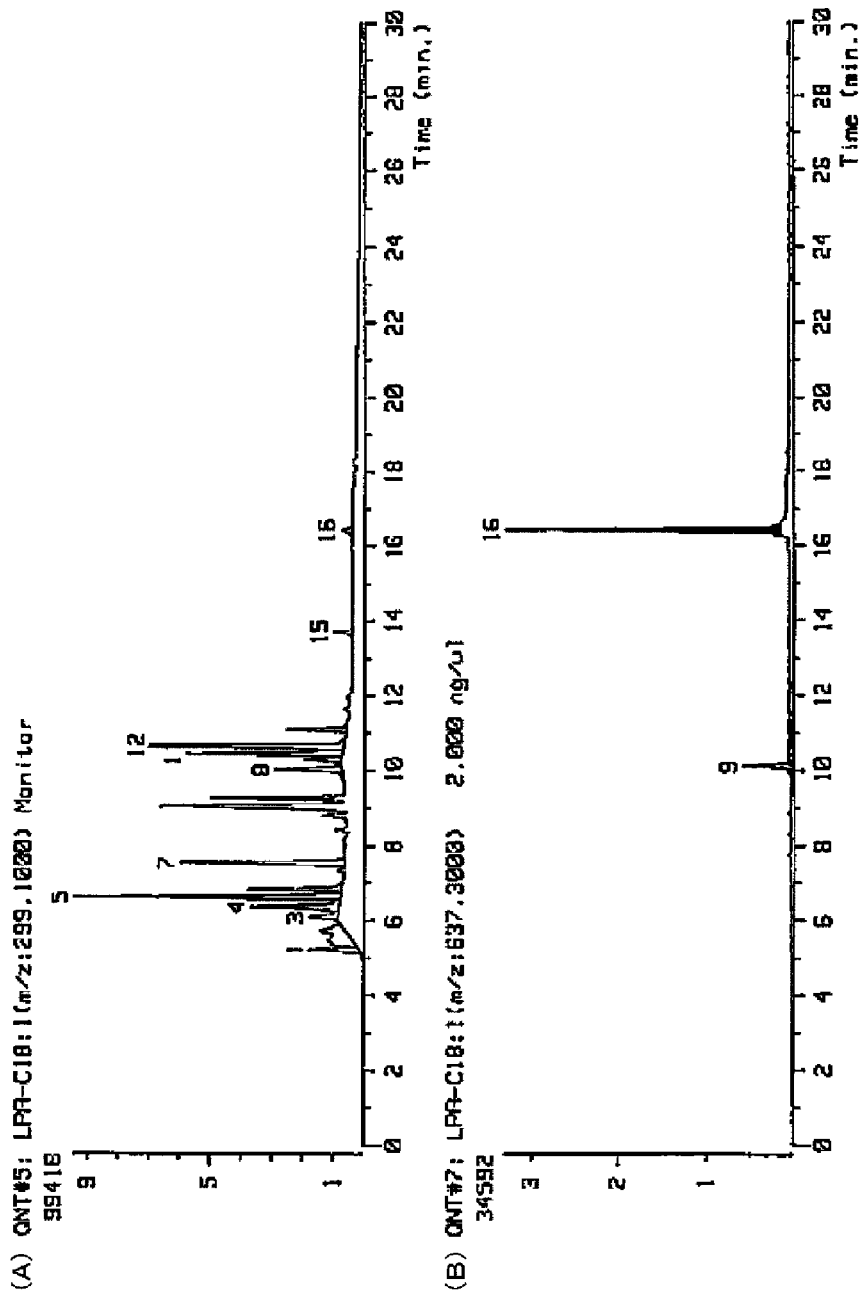
[FIG. 1-1] A chart showing the result of GC-SIM analysis of a LPA-C18:1 standard sample. (A) GC-SIM analysis at the m/z value of 299.1, (B) GC-SIM analysis at the m/z value of 637.3.

In the supernatant of a culture obtained by culturing human embryos in a medium until they develop into blastocysts, as aforementioned, no such protein originating from the human embryo was detected as having an activity capable of influencing on implantation of a transferred blastocyst and pregnancy, whereas five particular lysophosphatidic acids were contained in the culture supernatant as the only ingredients originating from the human embryos. Therefore, those lysophosphatidic acids are the ingredients acting, either one of which alone, or some of them in cooperation, to stimulate the uterine endometrium and prepare the optimal environment for transfer of the blastocysts. The pregnancy-promoting agent according to the present invention is an agent which increases the success rate of implantation and pregnancy when injected into the uterine cavity of a patient prior to the transfer of a blastocyst in SEET therapy.

Patient to be treated with the pregnancy-promoting agent according to the present invention are mammalian animals, including, but not limited to, human in particular, and household such as bovine and horse, and pets such as dog and cat.

In the present invention, the term "lysophosphatidic acid" includes 1-acylglycerol 3-phosphate and 2-acylglycerol 3-phosphate, of which preferred is 1-acylglycerol 3-phosphate.

The term "Lysophosphatidic acids" according to the present invention includes compounds of the following structures (irrespective of either their free form or their salts). When they take salt forms, there is no particular limitation as to the species of cation $M^+$, but preferred are monovalent metal ions, such as alkali metal ions like those of Na and K and ammonium ions, of which Na ion is particularly preferred.

(1) LPA-C16:0

[Chem 1]

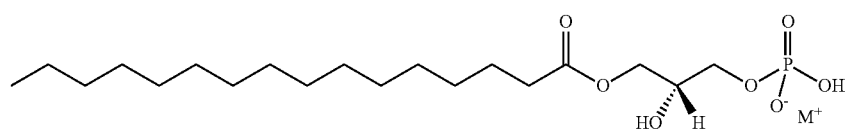

(1)

(2) LPA-C16:1

[Chem 2]

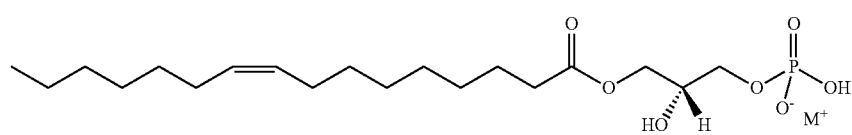

(2)

-continued (3) LPA-C18:0

[Chem 3]

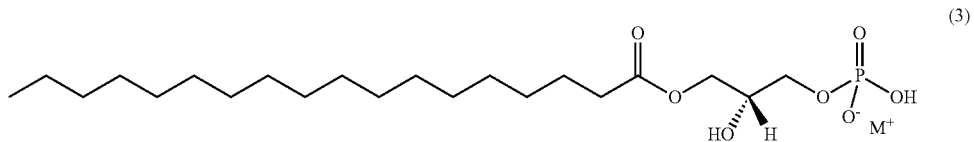

(4) LPA-C18:1

[Chem 4]

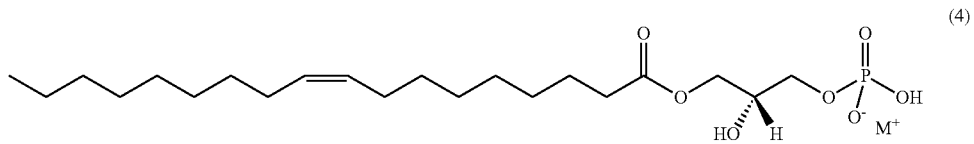

(5) LPA-C18:2

[Chem 5]

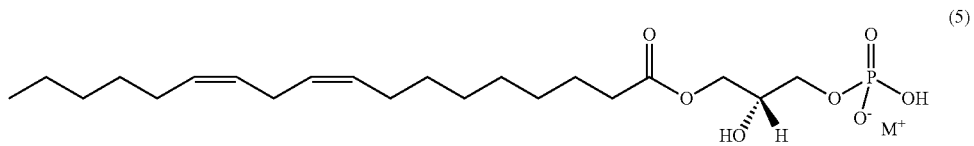

The pregnancy-promoting agent according to the present invention is a composition comprising one or more lysophosphatidic aids selected from the group consisting of five lysophosphatidic acids: LPA-C16:0, LPA-C16:1, LPA-C18:0, LPA-C18:1, and LPA-C18:2.

In the case where the pregnancy-promoting agent according to the present invention comprises all of these five lysophosphatidic acids, the pregnancy-promoting agent according to the present invention is prepared so that the molar ratio among LPA-C16:0, LPA-C16:1, LPA-C18:0, LPA-C18:1, and LPA-C18:2 contained therein falls in the range preferably of (LPA-C16:0) : (LPA-C16:1) : (LPA-C18:0) : (LPA-C18:1) : (LPA-C18:2)=36-66:1-2:5-10:13-25:15-28, more preferably of 46-56:1.3-1.7:5.9-8.0:17-21:19-23, still more preferably of 48-54:1.4-1.6:6.9-7.7:18-20:20-22, and is most preferably 51:1.5:7.3:19:21.2, as determined by the method for measurement on gas chromatography described in the Example section.

In the case where the pregnancy-promoting agent according to the present invention comprises all of these five lysophosphatidic acids, the pregnancy-promoting agent according to the present invention, if administered to a human, is prepared so that the amount of each lysophosphatidic acid for one time of administration might be 98-182 pmol for LPA-C16:0, 2.8-5.2 pmol for LPA-C16:1, 14-26 pmol for LPA-C18:0, 36-68 pmol for LPA-C18:1, and 40-76 pmol for LPA-C18:2; more preferably 126-139 pmol for LPA-C16:0, 3.6-4.4 pmol for LPA-C16:1, 18-22 pmol for LPA-C18:0, 47-57 pmol for LPA-C18:1, and 52-64 pmol for LPA-C18:2; still more preferably 133-147 pmol for LPA-C16:0, 3.8-4.2 pmol for LPA-C16:1, 19-21 pmol for LPA-C18:0, 49-55 pmol for LPA-C18:1, and 55-61 pmol for LPA-C18:2; most preferably 140 pmol for LPA-C16:0, 4 pmol for LPA-C16:1, 20 pmol for LPA-C18:0, 52 pmol for LPA-C18:1, and 58 pmol for LPA-C18:2; as determined by the method for measurement on gas chromatography described in the Example is section.

While the pregnancy-promoting agent according to the present invention may be prepared in the form of a composition comprising all the five lysophosphatidic acids, this is not a requisite and the agent may also be prepared in the form of a package in which each of the five lysophosphatidic acids is separately packed. Preparing the agent in the form of a package in which each of the five lysophosphatidic acids is separately packed would provide such an advantage that it would allow the dose of each lysophosphatidic acid be adjusted as desired when administered to a patient.

The pregnancy-promoting agent according to the present invention may be a composition which further comprises one or more of pharmaceutically acceptable, various additives as desired. Examples of such additives mainly include isotonizers, buffers, preservatives, stabilizers, pH adjusting agents, and the like.

The pregnancy-promoting agent according to the present invention can be obtained from the supernatant of a culture prepared by culturing an embryo of a mammalian animal in a medium until it develops into a blastocyst. Though there is no particular limitation as to an embryo of a mammalian animal, it is preferably an embryo of a human, household (bovine, horse, pig, sheep, goat, etc.) or a pet animal (dog, cat, etc.), and a human embryo is particularly preferred.

Though there is no particular limitation as to a medium in which an embryo of a mammalian animal is to be cultured, as far as it can be used in culturing an embryo, a serum-free medium is preferred to eliminate a risk of contamination with an infectious agent, such as prions, which could be brought in with bovine serum. A commercially available serum-free medium such as BlastAssist System 1 (MediCult, Jyllinge, Denmark) and BlastAssist System 2 (MediCult, Jyllinge, Denmark), for example, may be employed.

The five lysophosphatidic acids contained in the pregnancy-promoting agent according to the present invention can be chemically synthesized by a conventional method using glycerol 3-phosphate and fatty acids as raw materials. Therefore, it is also possible to prepare the pregnancy-promoting agent according to the present invention by blending the five different lysophosphatidic acids chemically synthesized.

The pregnancy-promoting agent according to the present invention obtained from the supernatant of a culture of embryos of a mammalian animal may be used as a pregnancy-promoting agent for the corresponding mammalian animal, and, as far as it proves effective, also as a pregnancy-promoting agent for other species of mammalian animals.

In order to improve success rate of pregnancy and implantation in blastocyst transfer, the pregnancy-promoting agent according to the present invention is administered by its injection into the uterine cavity of a recipient, prior to transfer of blastocysts into the uterus of the recipient. The timing of administration is preferably 1-5 days, and more preferably 2-4 days, before the transfer of blastocysts. Administration may be carried out only once (e.g., once 3 days before), or multiple times, daily or every other day.

EXAMPLES

Though the present invention will be described in further detail below with reference to an example, it is not intended that the present invention be limited to the example.

[Culture of Germ Cells]

Medication of the patients was started with 600 μg of a gonadotropin-releasing hormone (GnRH) agonist on day 7 before the hyperthermic phase in the cycle of SEET therapy, and then, on day 3 of menstruation and thereafter, daily stimulation of ovaries was given with follicle-stimulating hormone (FSH preparation or HMG preparation) until the size of the second leading follicles reached 18 mm in diameter. Ovulation was induced when the second leading follicles became greater than 18 mm in diameter. Ova were retrieved transvaginally under utrasonographic guidance 36 hours after intramuscular administration of 500 units of human chorionic gonadotropin (hCG). The follicles were measured by ultrasonic scanning (Mitsubishi RDF173H).

The ova thus retrieved were fertilized by insemination or intracytoplasmic sperm injection. The fertilized eggs were cultured in a 50-pL droplet of BlastAssist System medium 1 [containing synthetic serum replacement (SSR), human plasma albumin, glucose, sodium pyruvate, lactate, potassium sulfate, magnesium sulfate, sodium chloride, sodium hydrogen phosphate, non-essential amino acids, L-glutamine, taurine, sodium bicarbonate, HEPS, streptomycin 50 mg/L, penicillin 50,000 IU/L, and phenol red: MediCult, Jyllinge, Denmark] and early embryos were obtained on day 2. Then, one to four of the early embryos thus obtained were cultured in a 50-pL droplet of BlastAssist System medium 2 [containing synthetic serum replacement (SSR), human plasma albumin, glucose, sodium pyruvate, lactate, potassium sulfate, magnesium sulfate, sodium chloride, sodium hydrogen phosphate, essential amino acids, non-essential amino acids, L-glutamine, taurine, sodium bicarbonate, streptomycin 50 mg/L, penicillin 50,000 IU/L, and phenol red: MediCult, Jyllinge, Denmark], under a covering layer of mineral oil (Oil Embryo Culture, Irvine Scientific Santa Ana Calif. USA) for further three days, i.e., up to day 5 in total, to obtain blastocysts. The culture plates employed here were FALCON 353002 Tissue Culture Dish (Becton Dickinson, Franklin Lakes USA. The culture of the embryos were carried out in an incubator (TE-HER PRODUCT $O_2$-$CO_2$ incubator CP 02-1800 series, Hirasawa) set at 5% $CO_2$, 5% $O_2$, 90% $N_2$ 37 °C., and 100% humidity. The supernatant of the embryo culture was collected and stored at −20° C. until use in SEET therapy. The early embryos and the blastocysts were transferred to the patients.

(Pooling of Remaining Culture Supernatant of Embryos)

Of the culture supernatant of embryos of 45 patients who had received SEET therapy, remaining portions unused in the SEET therapy, were pooled and subjected for analysis. The volume of the remaining supernatant pooled was about 2.6 mL.

[Analysis of Proteinous Ingredients]

First, assuming that the active ingredient contained in the culture supernatant was some protein, like a peptide hormone, the concentrations of such proteins in the culture supernatant, including human chorionic gonadotropin (hCG), that could be thought to help improve the success rate of pregnancy in SEET therapy, were measured by ELISA. As a result, none of those proteins were detected in the supernatant of the embryo culture at all, indicating the active ingredient is a non-peptide compound.

[Analysis of LPA]

Then, as it had been known that the signal transduction via LPA3, one of lysophosphatidic acid receptors, plays an important role in implantation of a fertilized egg [Yo X. et.al., Nature (2005) 435, 104-108, (Non Patent Literature 17)], the content of LPA in the medium was measured by mass spectrometry.

LPA contained in the culture was extracted by Bligh-Dyer method. Namely, to 2.59 mL of an embryo culture were added 0.5 mL of purified water, 2.5 mL of methanol, and 1.25 mL of chloroform, and the mixture was gently stirred for about 10 seconds, to which were further added 1.0 mL of 0.5 M HCl (prepared using saturated saline) and 2.5 mL of chloroform, and after stirring for one minute, the mixture was centrifuged (10 min, 3000 rpm, 4° C.) into separate layers, of which the lower, chloroform layer was collected. To the water layer was added 2.5 mL of chloroform, and after stirring and centrifugation in the above-described manner, the lower, chloroform layer was collected. These chloroform layers collected were combined and the solvent was removed under nitrogen gas flow. Unused BlastAssist System medium 2 was treated in the same manner as a blank.

To the residue which remained after removal of the solvent were added pyridine and BSTFA [N,O-bis(trimethylsilyl)trifluoroacetamide solution containing 1% chlorotrimethylsilane], 25 pL each, to suspend the residue, and reaction was allowed at 70° C. for one hour. The reaction mixture was subjected to GC-SIM analysis and GC-MS(Scan).

Separately, LPA-C18: 1 [oleyl-L-a-lysophosphatidic acid sodium salt (Sigma-Aldrich)] was dissolved in methanol at a concentration of 1 mg/mL to prepare a standard solution. The standard solution was diluted with unused BlastAssist System 2 (blank solution) as needed and extracted by Bligh-Dyer method, and then, after addition of pyridine and BSTFA, 25 μL each, to form a suspension, reaction was allowed at 70° C. for one hour, and then the reaction mixture was subjected to GC-SIM analysis and GS-MS(Scan) to determine the detection limit value and produce a standard curve for quantitative determination of LPA.

GC-SIM analysis was carried out using JMS-700V (JEOL Ltd.), a mass spectroscope (MS apparatus), and HP-6890 (Agilent Technologies Inc.), a gas chromatography apparatus (GC apparatus). The GC column employed was SPB-1 (SUPELCO). The column was kept at 150° C. for 1 minute, and the temperature was raised to 300° C. linearly at the rate of 10° C./min, and was kept at 300° C. for 25 minutes. Helium, a carrier gas, was supplied to the column at a linear velocity of 30 cm/sec. The temperature of the injection port was set at 250° C., and 1 μL of a sample was injected (Splitless injection). The sample was ionized by the electron impact (EI) method under the condition in which the temperature of the ionization chamber was set at 250° C., the ionization voltage at 70 eV, and the ionization current at 100 pA. The detector of the MS apparatus was the double-focusing type (BE type) and the acceleration voltage was 10 kV.

Lysophosphatidic acid, when ionized by the electron impact (EI) method, give rise to an ion attributable to glycerol 3-phosphate moiety and ions attributable to fatty acid moieties. The m/z value for the ion attributable to glycerol 3-phosphate moiety is 299.1. Meanwhile, the m/z values for the ions (ions for detection) attributable to fatty acid moieties vary depending on each species of fatty acids as listed in Table 1. In addition, there are characteristic ions attributable to LPA: an ion with m/z value of 129.1, which is attributable to glycerol-TMS, and an ion with m/z value of 73.1, which is attributable to freed TMS. Accordingly, GC-SIM and GC-MS (Scan) analyses were carried out in the m/z value ranging 35-800. Besides, a m/z value means the value formed by dividing the mass "m" of an ion by its charge number (mass-to-charge ratio).

TABLE 1 m/z values for detected ions attributed to lysophosphatitic acids in GC-SIM analysis

| Names of Compound | m/z values |
| --- | --- |
| LPA-C14:0 | 583.3 |
| LPA-C16:0 | 611.3 |
| LPA-C16:1 | 609.3 |
| LPA-C18:0 | 639.4 |
| LPA-C18:1 | 637.3 |
| LPA-C18:2 | 635.3 |
| LPA-C18:3 | 633.3 |
| LPA-C20:0 | 667.4 |
| LPA-C20:1 | 665.4 |
| LPA-C20:2 | 663.4 |
| LPA-C20:3 | 661.4 |
| LPA-C20:4 | 659.3 |
| LPA-C20:5 | 657.3 |
| LPA-C20:6 | 685.4 |

Figures 1, 2:
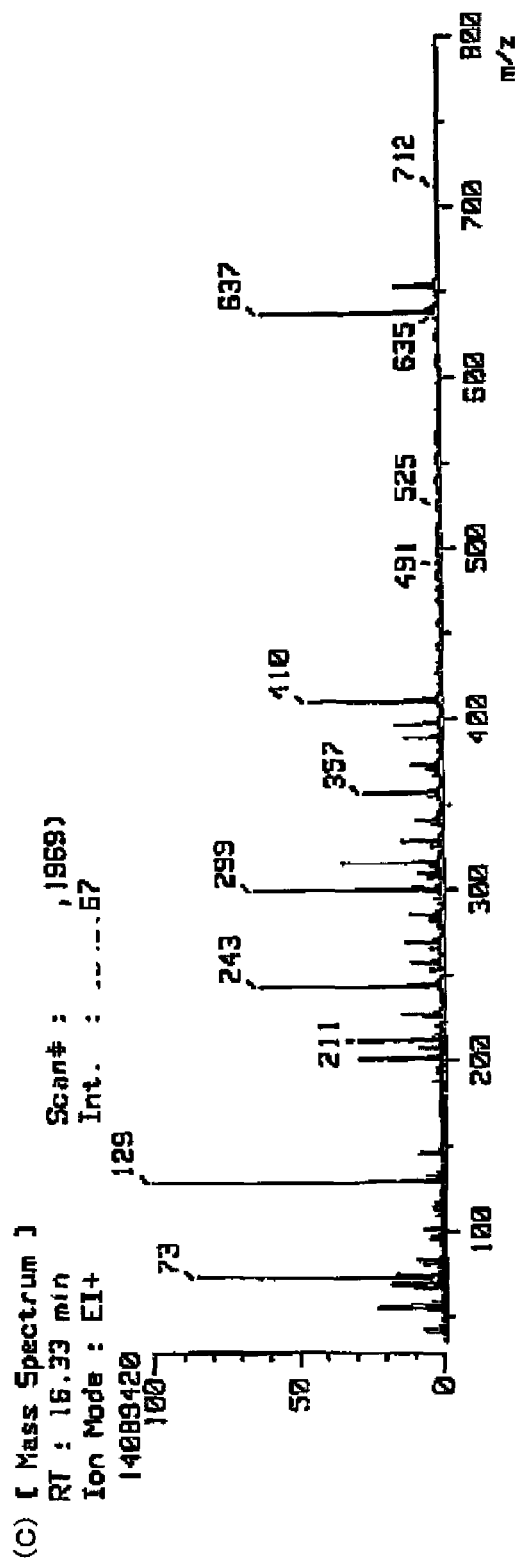
Figures 1, 2:
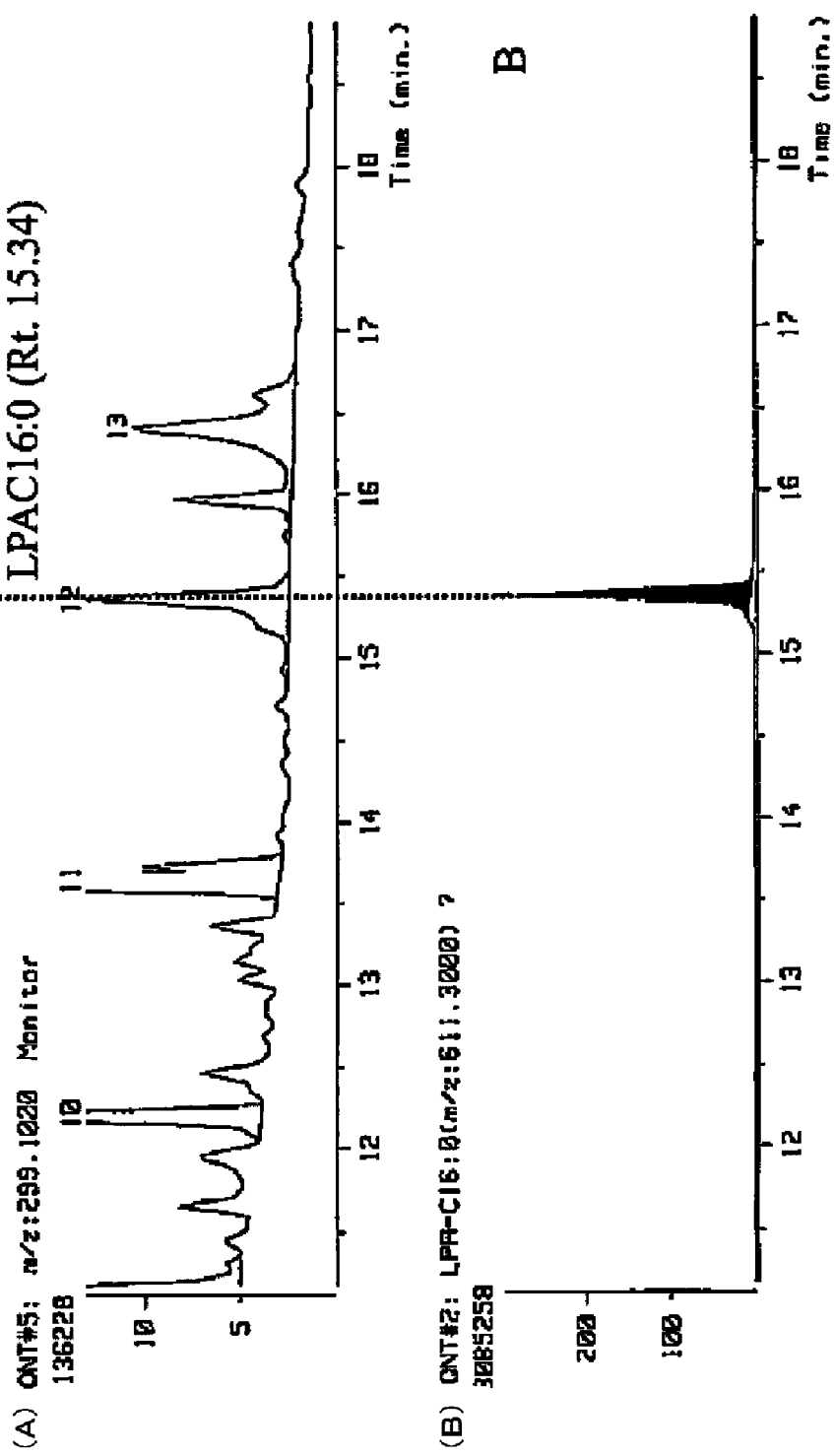
Figure 2:
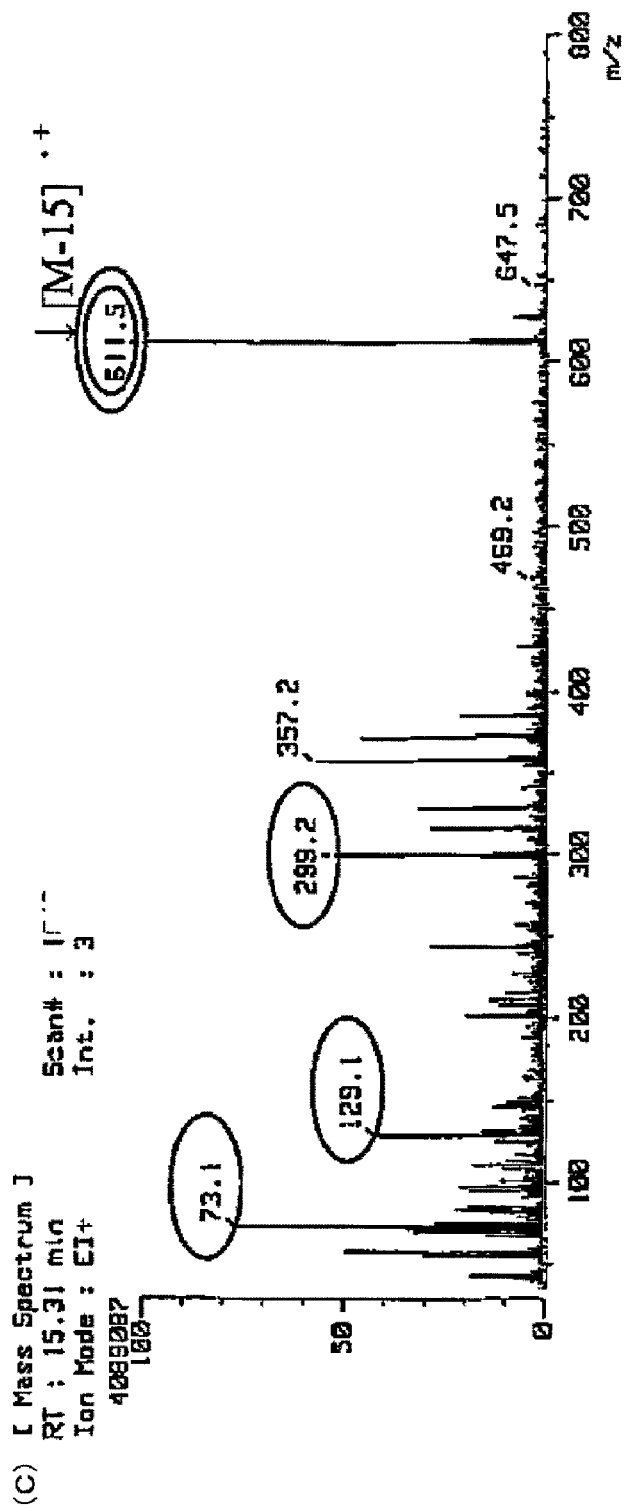

GC-SIM analysis of a dilution of the standard solution containing LPA-C18:1 gave a peak, at a retention time of 16.33 minutes, with m/z value of 637.3, which corresponded to an ion for detection of LPA-C18:1, and also a peak with m/z value of 299.1, which was attributed to glycerol-3-phosphate moiety (FIG. 1-1, A and B). Further, GC-MS(Scan) analysis, at the retention time of 16.33 minutes, gave peaks with m/z values of 299.1 and 637.3, as well as peaks with m/z values of 129 (129.1) and 73 (3.1), which were characteristic of LPA, demonstrating that LPA-C18:1 contained in the standard was measured with accuracy by mass spectrometry (FIG. 1-2, C).

Then, the samples were subjected to GC-SIM analysis. LPA-C16:0 was analyzed first. As a result, it gave, at a retention time of 15.31 minutes, a peak with m/z value of 611.3, which corresponded to the ion for detection of LPA-C16:0, as well as a peak with m/z value of 299.1, attributed to the glycerol 3-phosphate moiety (FIG. 2-1, A and B). Furthermore, GC-MS(Scan) analysis, at the retention time of 15.31 minutes, gave peaks with m/z value of 299.1 and 611.3, as well as peaks with m/z values of 129 (129.1) and 73 (73.1), which were characteristic of LPA (FIG. 2-2C), confirming that the sample contained LPA-C16:0.

Figures 1, 3:
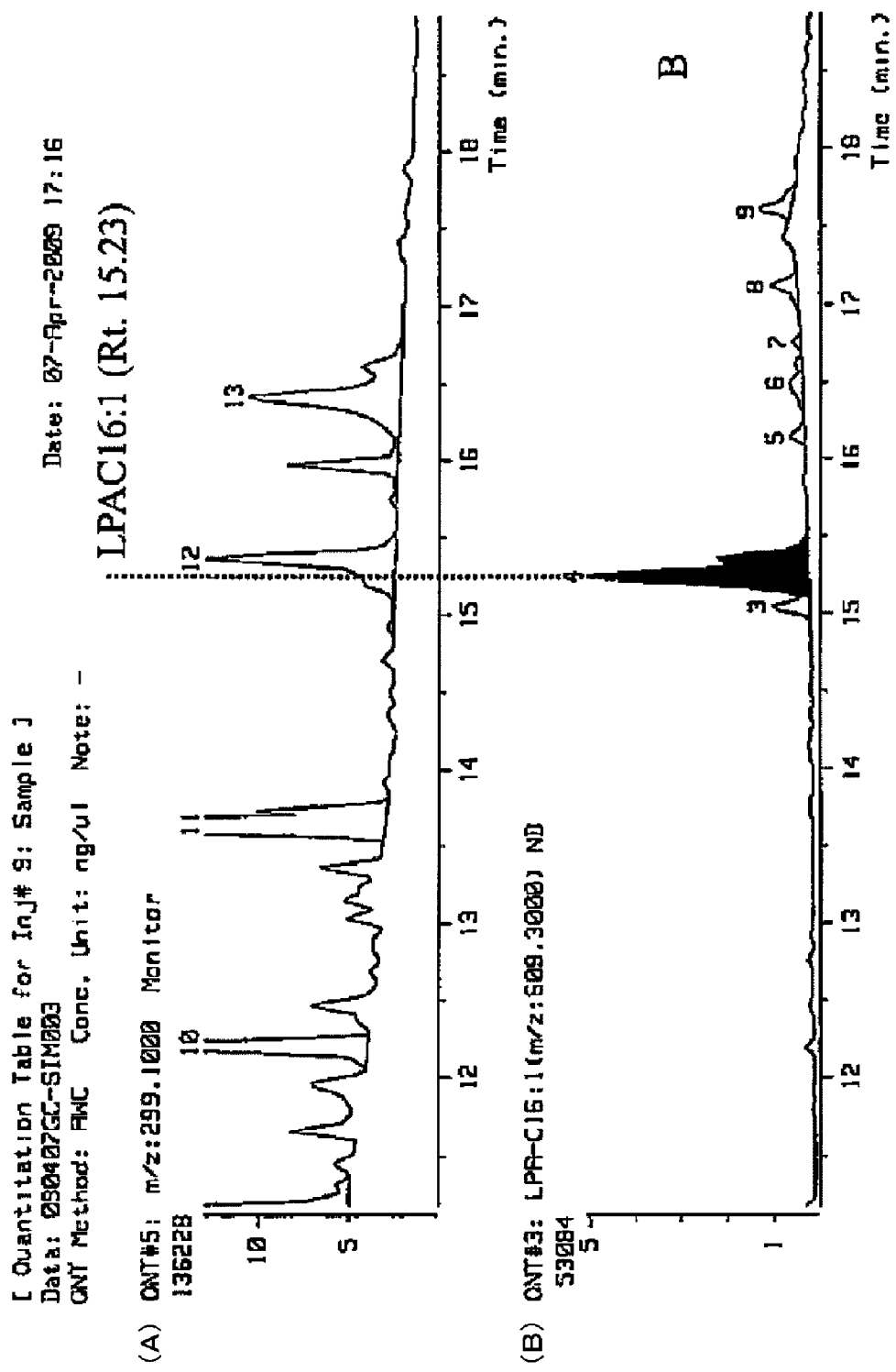
Figures 2, 3:
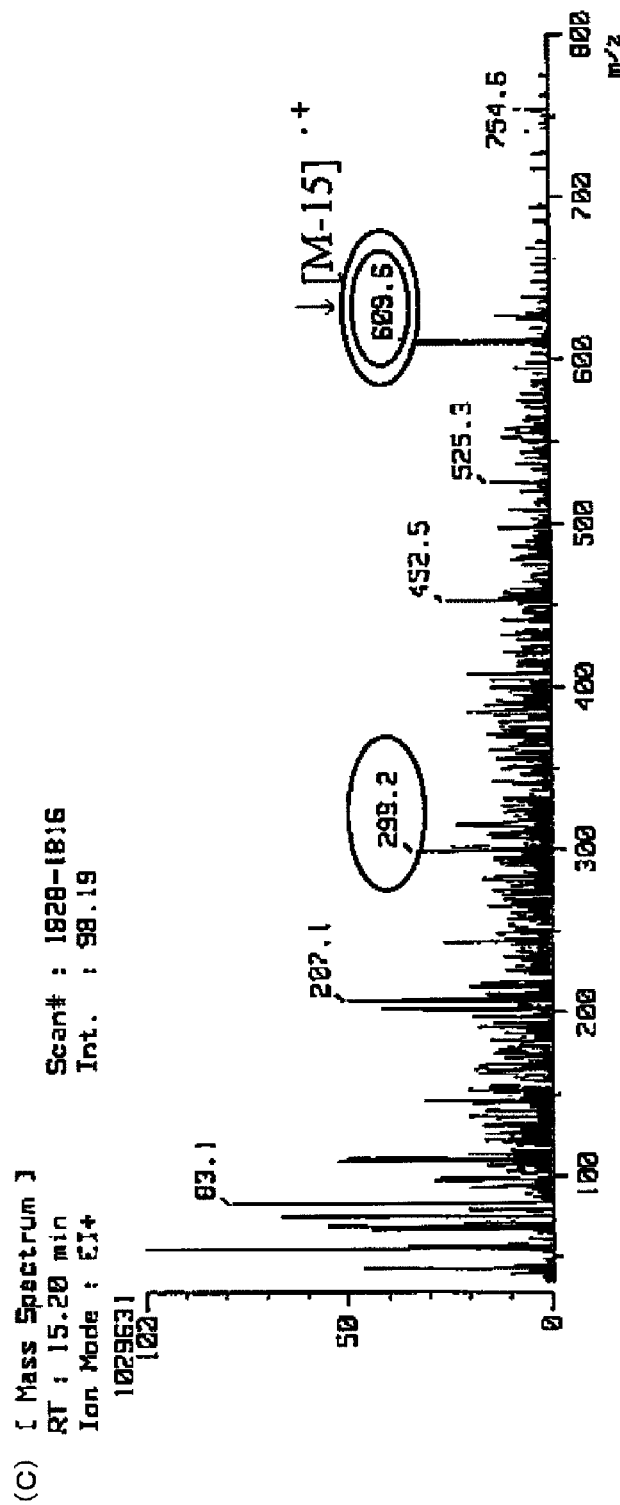

Then, GC-SIM analysis was carried out for LPA-C16:1. As a result, it gave, at a retention time of 15.20 minutes, a peak with m/z value of 609.3, which corresponded to the ion for detection of LPA-C16:1, as well as a peak with m/z value of 299.1, attributed to the glycerol 3-phosphate moiety (FIG. 3-1, A and B). Furthermore, GC-MS(Scan) analysis, at the retention time of 15.20 minutes, gave peaks with m/z values of 299.1 and 609.3 (FIG. 3-2, C), confirming that the sample contained LPA-C 16:1. Furthermore, GC-MS(Scan) analysis, though not clear due to noises, gave signals considered to be peaks with m/z values of 129 (129.1) and 73 (73.1), which were characteristic of LPA.

Figures 1, 4:
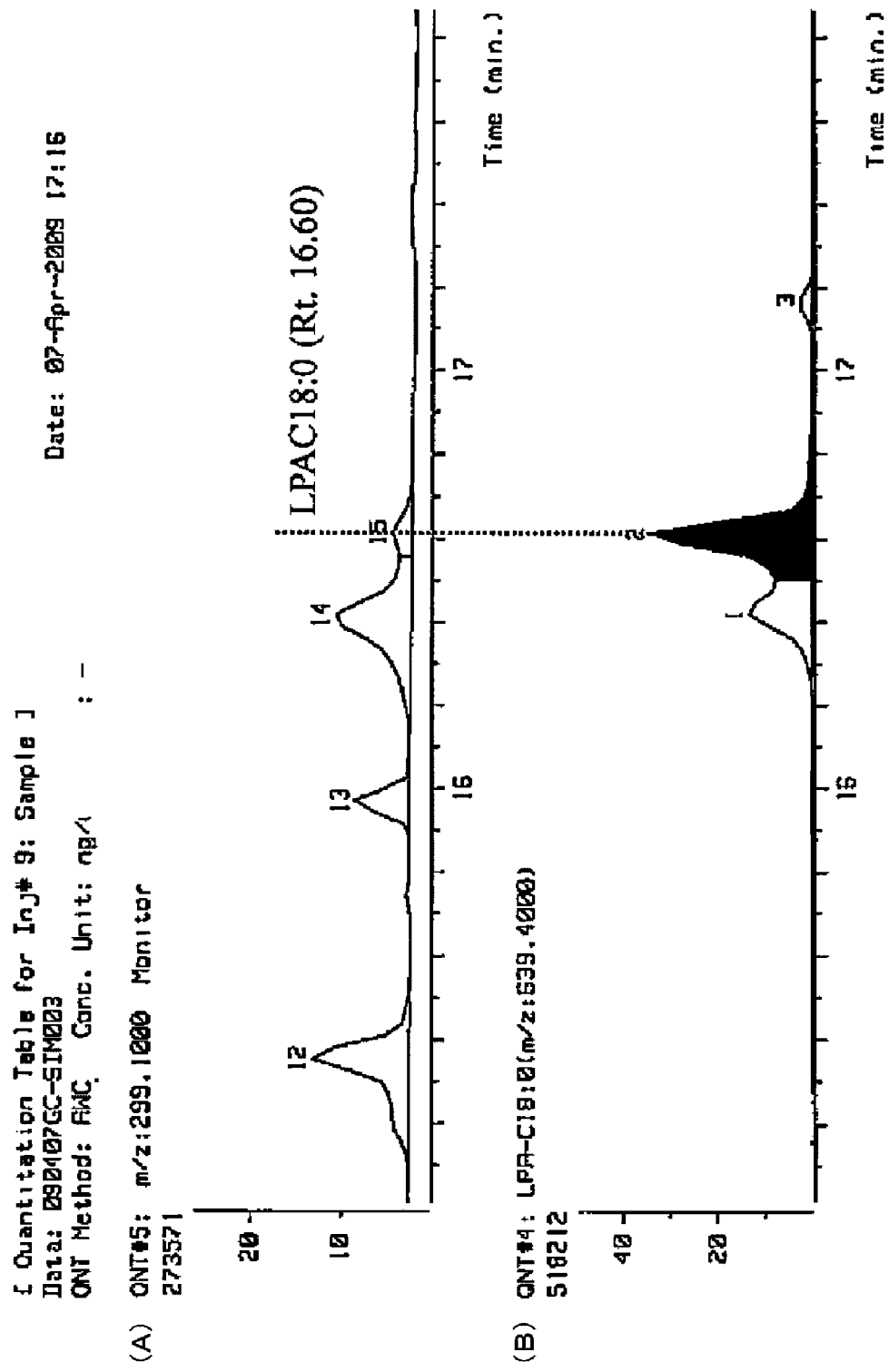
Figures 2, 4:
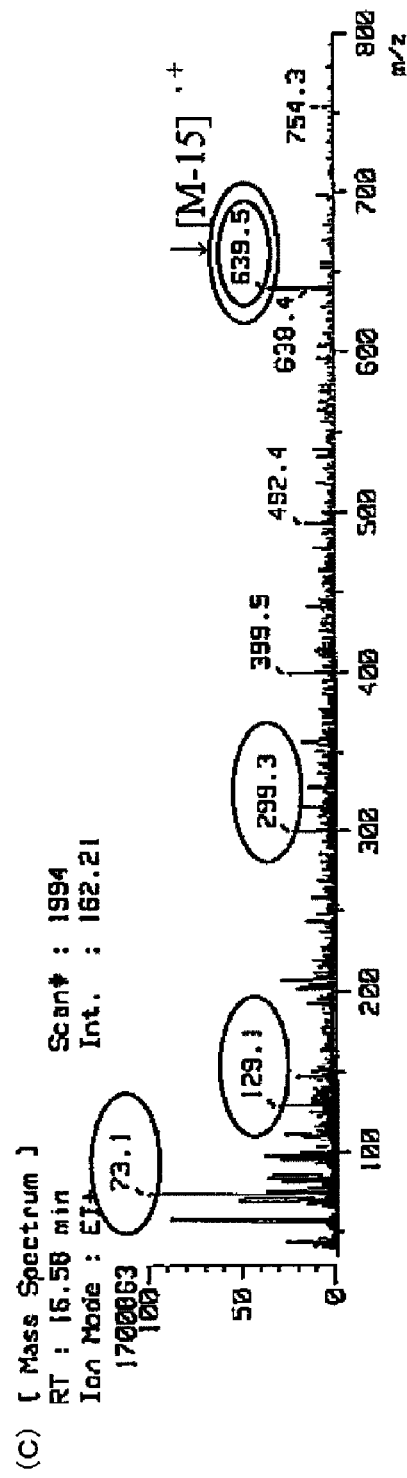

Then, GC-SIM analysis was carried out for LPA-C18:0. As a result, at a retention time of 16.58 minutes, it gave a peak with m/z value of 639.4, which corresponded to the ion for detection of LPA-C18:0, as well as a peak with m/z value of 299.1, attributed to the glycerol 3-phosphate moiety (FIG. 4-1, A and B). Furthermore, GC-MS(Scan) analysis, at the retention time of 16.58 minutes, gave peaks with m/z values of 299.1 and 639.4, as well as peaks with m/z values of 129 (129.1) and 73 (73.1), which were characteristic of LPA (FIG. 4-2, C), confirming that the sample contained LPA-18:0.

Figures 1, 5:
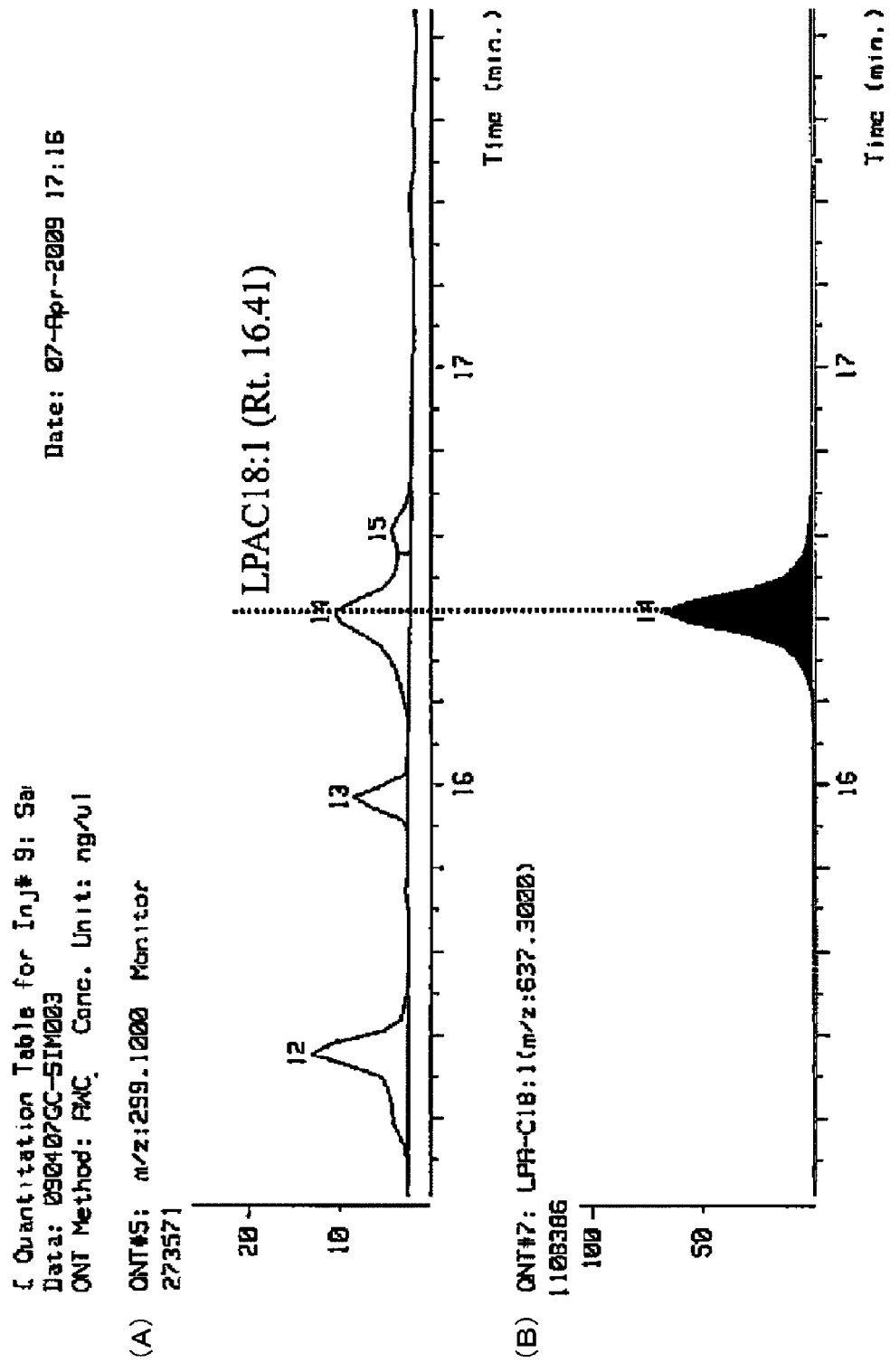
Figures 2, 5:

Then, GC-SIM analysis was carried out for LPA-C18:1. As a result, at a retention time of 16.39 minutes, it gave a peak with m/z value of 637.3, which corresponded to the ion for detection of LPA-C18:1, as well as a peak with m/z value of 299.1, attributed to the glycerol-3 phosphate moiety (FIG. 5-1, A and B). Furthermore, GC-MS(Scan) analysis, at the retention time of 16.39 minutes, gave peaks with m/z values of 299.1 and 637.3, as well as peaks with m/z values of 129 (129.1) and 73 (73.1), which were characteristic of LPA (FIG. 5-2, C), confirming that the sample contained LPA-C18: 1.

Figures 1, 6:
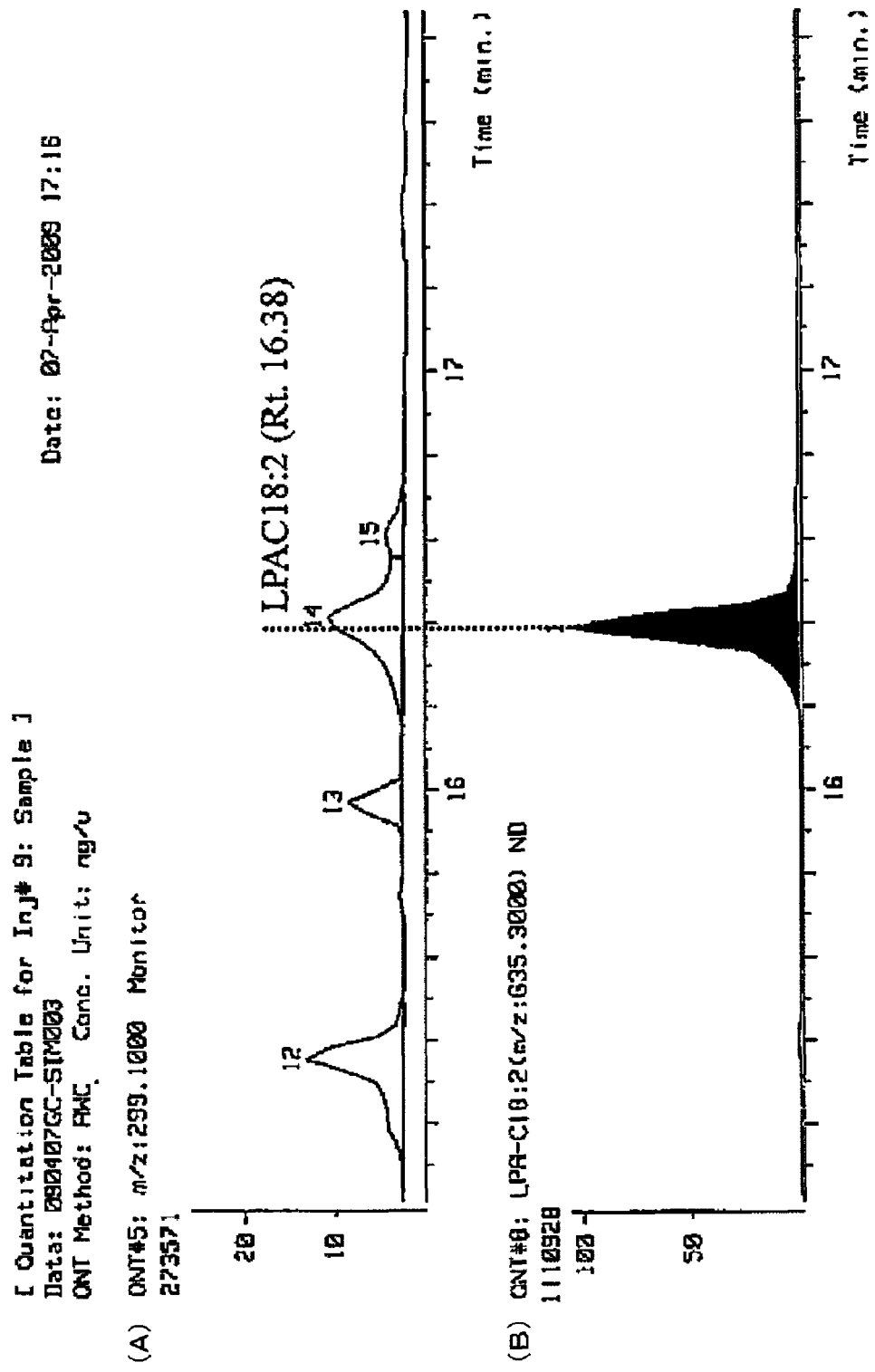
Figures 2, 6:
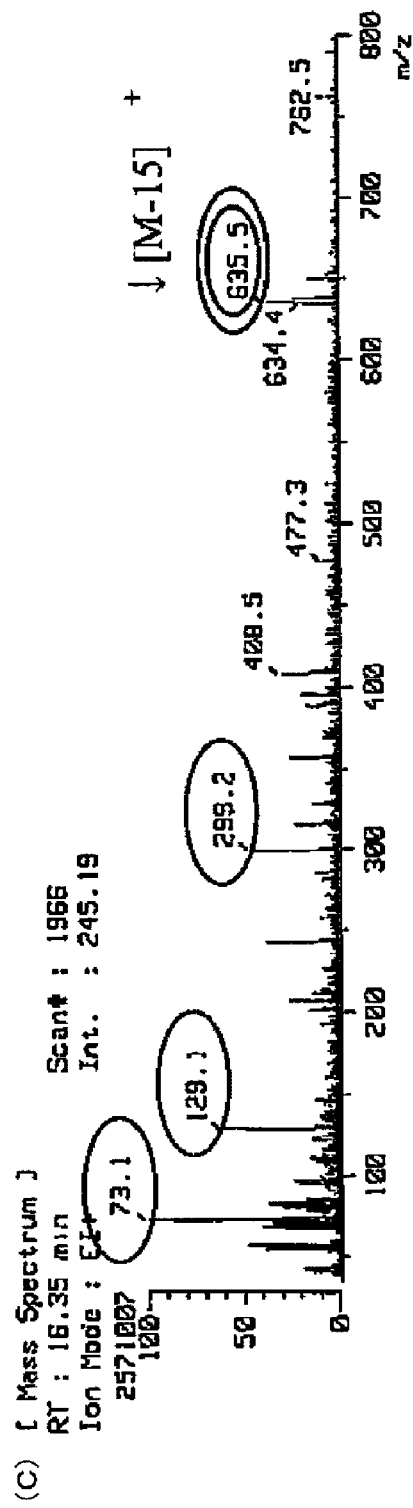

Then, GC-SIM analysis was carried out for LPA-C18:2. As a result, at a retention time of 16.35 minutes, it gave a peak with m/z value of 635.3, attributed to the detected peak of LPA-18:2, as well as a peak with m/z value of 299.1, attributed to the glycerol-3 phosphate moiety (FIG. 6-1, A and B). Furthermore, GC-MS(Scan) analysis, at the retention time of 16.35 minutes, gave peaks with m/z values of 299.1 and 635.3, as well as peaks with m/z values of 129 (129.1) and 73 (73.1), which were characteristic of LPA (FIG. 6-2, C), confirming that the sample contained LPA-C18:2.

Now, under the conditions for gas chromatography in the mass spectrometry carried out above, the compounds were eluted in the order of their boiling points. Thus, in the analysis of LPA, it was expected that, theoretically, they would be eluted in such an order that the shorter the carbon chain of the fatty acid moiety of an LPA was, the faster would it come out, and that, among those having carbon chains of the same length, one having the greater number of unsaturated bonds would come out the faster. Thus, comparison in the retention time of the ions for detection corresponding to LPA-C16:0, LPA-C16:1, LPA-C18:0, LPA-C18:1 and LPA-C18:2, i.e., 15.31 minutes for LPA-C16:0, 15.23 minutes for LPA-C16:1, 16.58 minutes for LPA-C18:0, 16.39 minutes for LPA-C18:1, and 16.35 minutes for LPA-C18:2, showed that their retention time was LPA-C16:1 <LPA-C16:0<LPA-C18:2<LPA-C18: 1<LPA-C 18:0, confirming that the result agreed with the theory.

Figures 1, 7:
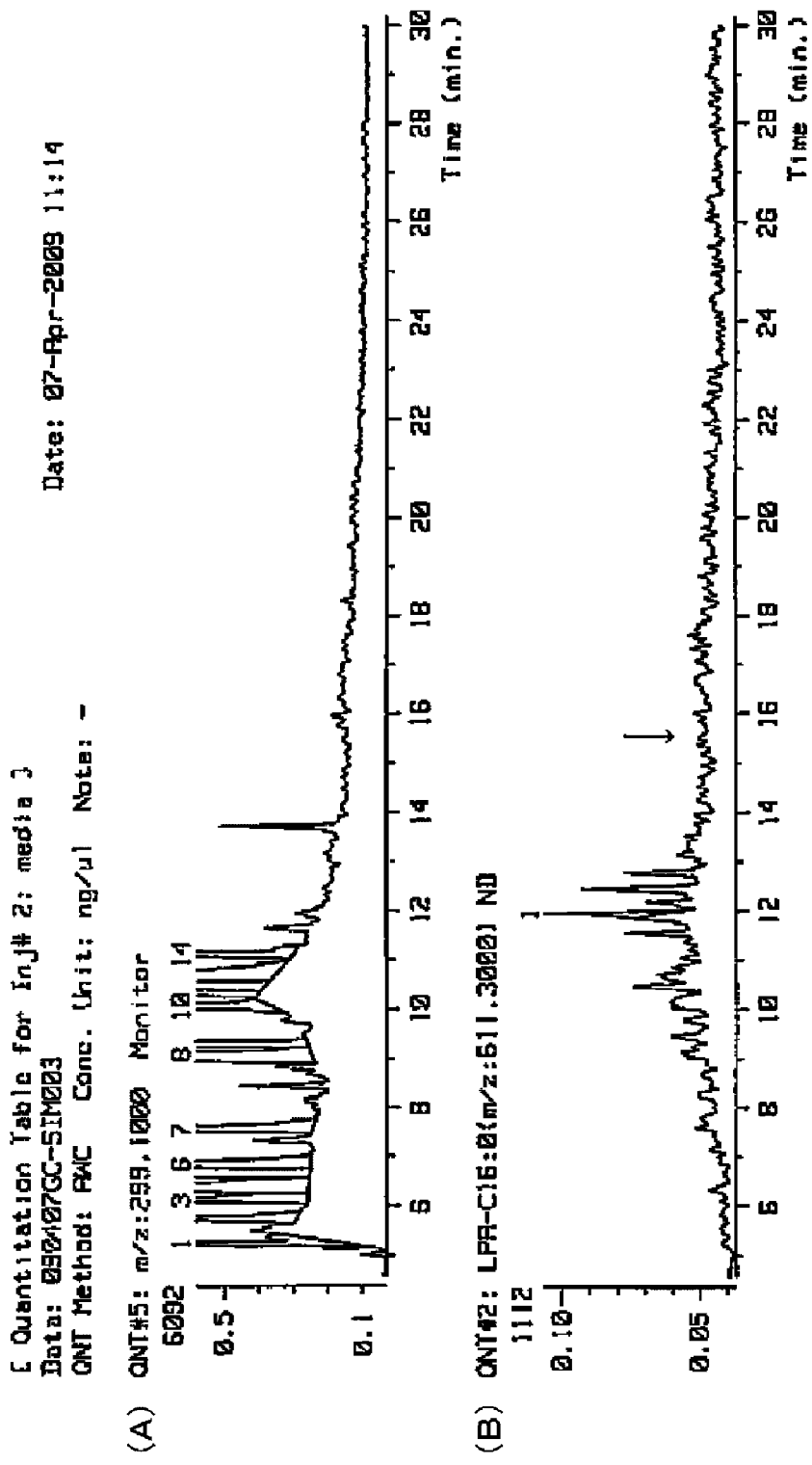
Figures 2, 7:
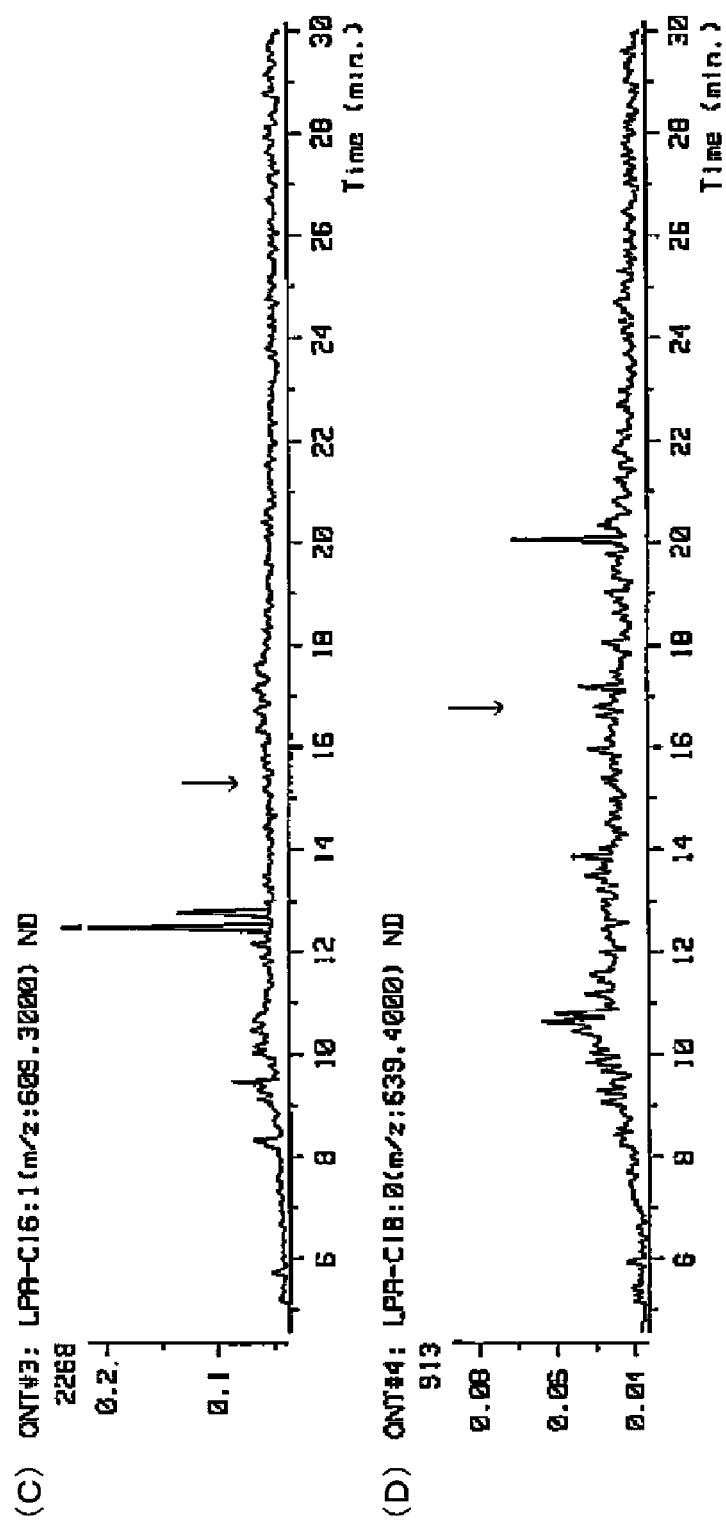
Figures 3, 7:
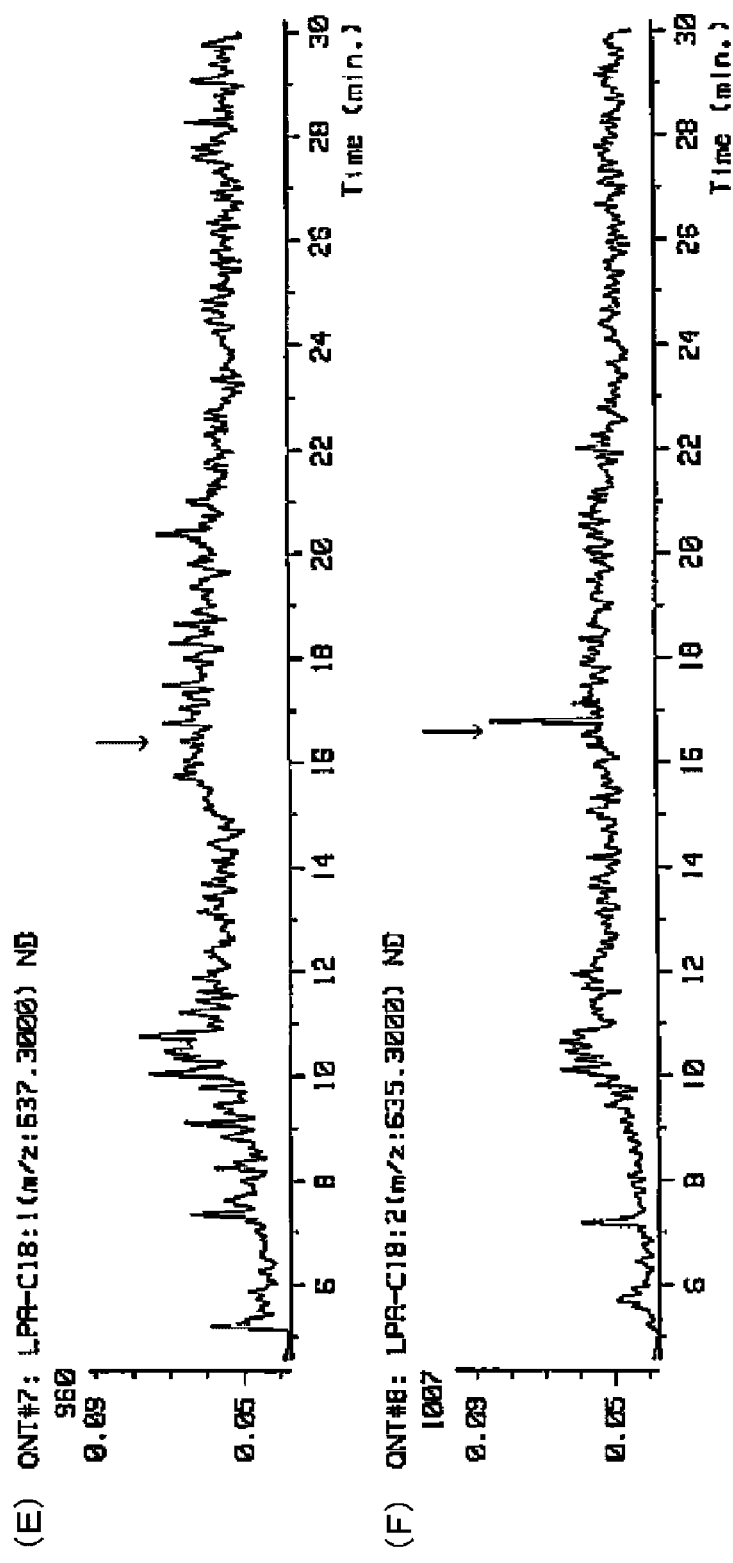

Though analysis was also carried out for other lysophosphatidic acids, no ions attributable to them were observed. Further, GC-SIM analysis of the blank solution revealed that no peak was detected that was attributable to LPA-C 16:0, LPA-C 16:1, LPA-C18:0, LPA-C18:1 and LPA-C18:2 (FIG. 7-1, A and B, FIG. 7-2, C and D, and FIG. 7-3, E and F).

From the above results, it is evident that the five lysophosphatidic acid, i.e., LPA-C16:0, LPA-C16:1, LPA-C18:0, LPA-C18:1 and LPA-C18:2, were contained in the supernatant of the embryos culture. And, putting together with the result of analysis for proteinous ingredients, it was revealed that the compound that were characteristically present in the supernatant of the embryo culture, in comparison with the blank solution (unused BlastAssist System medium 2), were those 5 lysophosphatidic acids alone. These findings indicate that the ingredients that promote pregnancy, which are contained in the supernatant of the embryo culture administered to the patient in SEET to promote pregnancy, are those 5 lysophosphatidic acids.

[Quantitative Determination of Lysophosphatidic Acids]

The concentration of each lysophosphatidic acid was measured based on the ratio of the area of the detected peak obtained by the analysis of the sample to that of the detected peak obtained by the analysis of the standard solution containing a known amount of LPA-C18:1. The results of measurement are shown in Table 2. As the volume of the culture supernatant injected into the uterine cavity in SEET therapy is about 20 pL, the amount of the lysophosphatidic acids administered at one time is about 140 pg for LPA-C16:0, about 4 pg for LPA-C16:1, about 20 pg for LPA-C18:0, about 52 pg for LPA-C18:1, and about 58 pg for LPA-C18:2.

TABLE 2

Concentration of lysophosphatidic acids contained in the sample

|  | LPA-C16:0 | LPA-C16:1 | LPA-C18:0 | LPA-C18:1 | LPA-C18:2 |
| --- | --- | --- | --- | --- | --- |
| Concentration (nmol/mL) | 7.0 | 0.2 | 1.0 | 2.6 | 2.9 |

INDUSTRIAL APPLICABILITY

The present invention is useful as agents for promoting pregnancy in fertility treatment of mammals with blastocyst transfer.

The invention claimed is:

1. A pregnancy-promoting agent for promoting pregnancy of a patient undergoing blastocyst transfer, comprising a mixture of the lysophosphatidic acids
LPA-C16:0, LPA-C16:1, LPA-C18:0, LPA-C18:1 and LPA-C18:2 and
wherein the mutual proportion of the content of LPA-C16:0, LPA-C16:1, LPA-C18:0,LPA-C18:1 and LPA-C18:2 is 36-66 : 1-2 : 5-10 : 13-25 : 15-28 in molar ratio.

2. A pregnancy-promoting agent according to claim 1, wherein the mutual proportion of the content of LPA-C16:0, LPA-C16:1, LPA-C18:0, LPA-C18:1 and LPA-C18:2 is 48-54 : 1.4-1.6 : 6.9-7.7 : 18-20: 20-22 in molar ratio.

3. A pregnancy-promoting agent according to claim 2, wherein the mutual proportion of the content of LPA-C16:0, LPA-C16:1, LPA-C18:0, LPA-C18:1 and LPA-C18:2 is 51 : 1.5 : 7.3 : 19 : 21.2.

* * * * *